US006923318B1

(12) United States Patent
Erickson et al.

(10) Patent No.: US 6,923,318 B1
(45) Date of Patent: Aug. 2, 2005

(54) SHARPS CONTAINER FOR SAFE STORAGE OF USED PEN NEEDLES AND USED MEDICAL SYRINGES

(75) Inventors: Thomas E. Erickson, Crosslake, MN (US); James J. Erickson, Mound, MN (US); Timothy A. Bachman, Saint Paul, MN (US)

(73) Assignee: Ulti Med, Inc, St. Paul, MN (US)

( * ) Notice: Subject to any disclaimer, the term of this patent is extended or adjusted under 35 U.S.C. 154(b) by 35 days.

(21) Appl. No.: 10/862,621

(22) Filed: Jun. 7, 2004

(51) Int. Cl.[7] .............................................. B65D 85/24
(52) U.S. Cl. ..................................... 206/366; 206/370
(58) Field of Search ............................... 206/363–366, 206/370; 220/908; 221/36, 37, 40, 45, 101; 604/110, 403

(56) References Cited

U.S. PATENT DOCUMENTS

| 5,046,614 A | * | 9/1991 | Torres et al. | ............... 206/366 |
| 5,409,113 A | | 4/1995 | Richardson et al. | |
| 5,469,964 A | * | 11/1995 | Bailey | ......................... 206/370 |
| 5,494,158 A | | 2/1996 | Erickson | |
| 5,545,145 A | | 8/1996 | Clinton et al. | |
| 5,603,404 A | * | 2/1997 | Nazare et al. | .............. 206/366 |
| 5,971,966 A | | 10/1999 | Lav | |
| 6,685,017 B2 | | 2/2004 | Erickson | |
| 6,745,898 B2 | * | 6/2004 | Lin | ............................ 206/366 |
| 6,792,662 B2 | * | 9/2004 | Samuel | ....................... 604/110 |

* cited by examiner

Primary Examiner—Luan K. Bui
(74) Attorney, Agent, or Firm—Roger W. Jensen

(57) ABSTRACT

A sharps container for safe reception and storage of used pen needles and used medical syringes comprises a housing which supports a manually rotatable member. A used pen needle receiving and ejecting apparatus is connected to the rotatable member. Used pen needles are inserted into the receiving apparatus. As the receiving and ejecting apparatus is rotated, a cam follower connected to the ejecting apparatus engages a cam within the housing to cause the ejection of the used pen needle from the receiving apparatus into the housing. The rotatable member also has an elongated recess sized to receive a medical syringe. Manual rotation of the rotatable member rotates the elongated recess to drop the medical syringe into the housing.

16 Claims, 4 Drawing Sheets

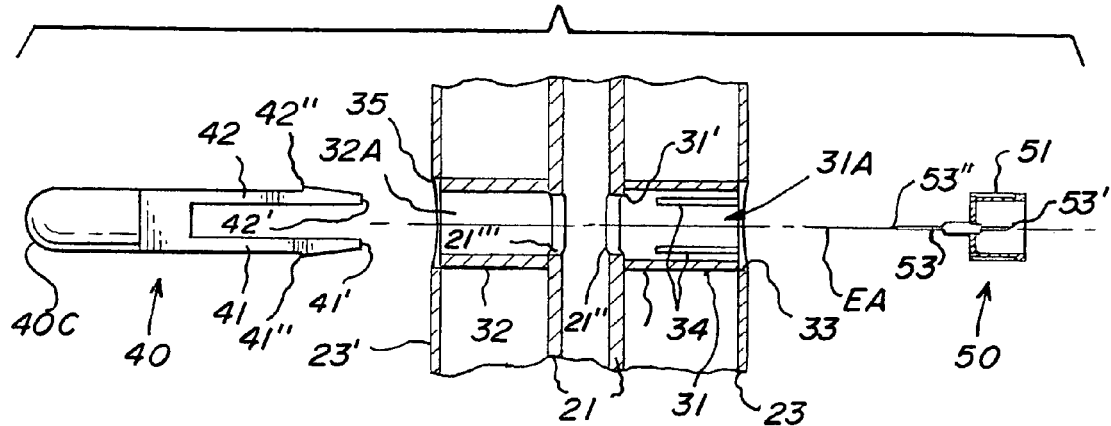
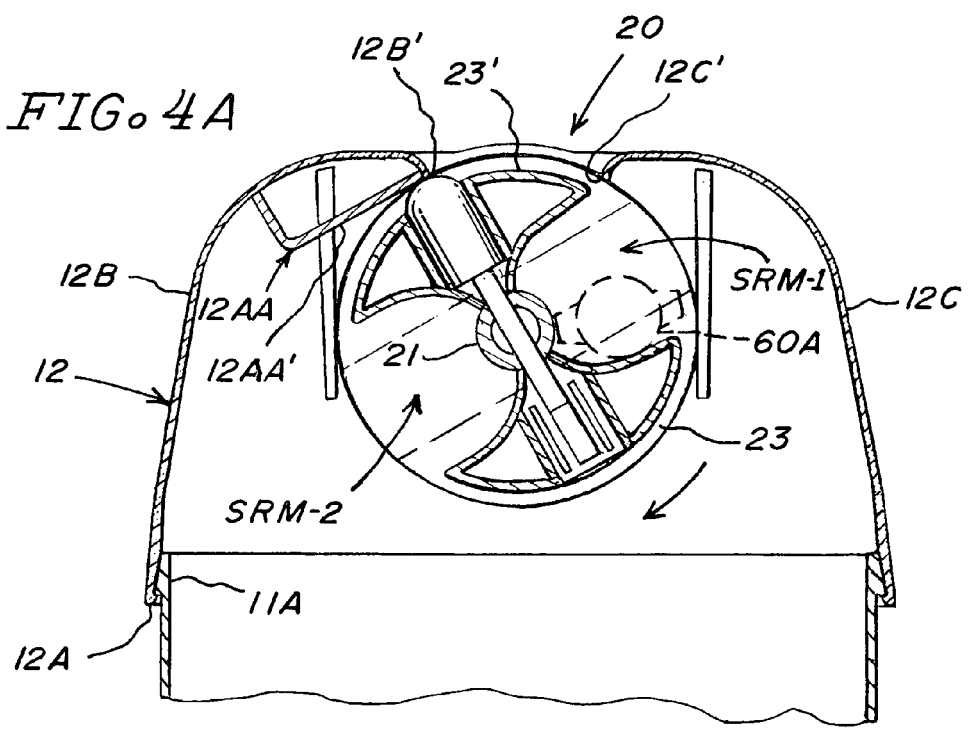

US 6,923,318 B1

SHARPS CONTAINER FOR SAFE STORAGE OF USED PEN NEEDLES AND USED MEDICAL SYRINGES

BACKGROUND AND FIELD OF THE INVENTION

This invention provides a "sharps" container for both used pen needles (sometimes hereafter referred to as "PNs") and used medical syringes (sometimes hereafter referred to as "MSs"). Pen needles are initially received by the user in the form of a pen needle assembly ("PNA").

Because of well known health issues, the safe disposal of "sharps" such as used pen needles, pen needle assemblies, and syringes has long been a high priority for medical related professional facilities. Prior art sharps containers are found in venues such as hospitals, medical clinics, and retail establishments. These containers are usually securely attached to a wall or other solid base means and have a lock means to permit controlled and safe removal of used "sharps."

However some containers are portable. Examples of prior art "portable" sharps containers for medical syringes are shown in U.S. Pat. Nos. 5,494,158 and 6,685,017.

Medical delivery pens (sometimes hereafter referred to as "MDPs") have become widely used in place of, or in addition to, medical syringes, e.g., by diabetics, who frequently inject themselves several times a day with accurately measured, adjustable, pre-selected amounts of insulin or other medication. Medical delivery pens include a reservoir of medication and a distal end adapted to be attached (usually by thread means) to a pen needle assembly (PNA). As is well known (see, for example, FIG. 1 of U.S. Pat. No. 5,545,145) the pen needle assembly has (within an outer, generally cylindrical shield 28) a generally cylindrical housing 26 within which is mounted an axially extending hollow needle 21, (i) the proximal end 24 of which punctures a seal in the distal end 16 of the medical delivery pen 10 (to allow the flow there-through of medication) when the delivery pen is screwed into the proximal end of the pen needle cylindrical housing 26, and (ii) the distal end 22 of which is for insertion into tissue of the person requiring the medication. The pen needle assemblies typically also include (i) a removable thin sterile seal covering the proximal (large diameter) end of the outer shield and (ii) a removable tube-like shield covering the distal portion of the hollow needle. The pen needle assembly is then factory sterilized. The user of a pen needle assembly removes the seal from the outer shield, screws the pen into the proximal end of the pen needle housing, removes the outer and tube-like shields, sets the medical delivery pen for the desired dose of medication, and then inserts the distal end of the pen needle into the target tissue following which the medical delivery pen is actuated to deliver the desired dose of medication through the hollow needle into said tissue.

Many diabetics routinely administer medication to themselves several times a day by injection of a pre-selected quantity of insulin (or substitute medication) in liquid form; the correct amount of medication can be determined from prior professional medical instruction or by use of convenient portable blood analysis kits which are small, compact and provide rapid indicators of the user's blood sugar level. Some of the typical several daily injections are often done away from the diabetic's residence which has made the use of the portable, convenient medical delivery pens widespread. The aforesaid testing kits and the medical delivery pens are relatively small in size and can easily fit within a woman's purse or equivalent. A typical scenario for a diabetic at a restaurant for a meal is to first use the blood sugar testing kit to obtain an indicator of his or her blood sugar level. This information then facilitates programming or adjusting the medical delivery pen to deliver the desired quantity of medication. Then the pen with an attached PN (a PNA sans the outer cylindrical and tube shields) is used to inject the tissue and dispense the medication. These steps require a relatively short length of time and can be done with minimum loss of privacy.

Some people requiring multiple daily medicine injections use both medical syringes and medical delivery pens with PNs.

MDPs are also widely used by doctors, nurses and other professionals in their duties. Many individuals will request (sometimes insist) that an injection be done with a pen needle rather than a syringe. The aforementioned professionals are especially mindful of possible dangers from a needle stick and the possible unwanted "sticks" that occur in the professional world.

In a perfect world, the user (both individual and professional) of a pen needle assembly would, after the first use of a pen needle, carefully detach the used PN from the medical delivery pen and safely dispose said PN into a safe sharps container. The approved disposal procedure is (i) insertion of the distal end of the needle into the tube-like shield (sometimes omitted) and thence the shielded needle and PN cylindrical housing into the outer cylindrical shield, (ii) unscrewing of the medical delivery pen from the proximal end of the pen needle cylindrical housing, and (iii) careful placement of the used pen needle assembly into a safe sharps container. Further, in the "perfect" world, the user of a medical syringe would safely dispose the used syringe into a safe sharps container.

Alas, the recommended safe disposal procedures are not always followed. Used (and potentially dangerous) syringes, PNs or PNAs are routinely left in unsafe places where third parties may unwittingly be "stuck" with possible dire consequences. Examples of such unsafe places are purses, the pockets on the back of aircraft seats, private and public wastebaskets, garbage receptacles, dumpsters and empty milk or other unsafe containers.

Further, the above described PNA or PN disposal procedure requires that the user (or associate) handle or hold the PN while the pen is unscrewed therefrom; this creates the possibility of a potentially dangerous "stick." Also, if the user (or associate) tries to insert the PN into the outer shield to form a PNA, then additional handling is again required with the possibility of a "stick".

The present invention provides a unique single sharps container having (i) a totally "no-touch" means for a user of a PNA to transfer a used PN from a pen into the container for safe storage therein without, as indicated, any touching of the used PN by the user, and (ii) a companion means for the safe storage of used medical syringes in the container.

SUMMARY OF THE INVENTION

This invention provides a unique sharps container for (i) safe manual, sequential disposing of used PNs into the container for safe storage therein and (ii) safe storage of used medical syringes in the same container using the same rotatable means which is used for the PN disposal. The container is a housing with an internal storage space sized to hold a plurality of used PNs and used medical syringes. A used PN receiving and ejecting means is provided within the housing and includes (i) manually rotatable means connected to the housing for rotation about an axis, (ii) an ejector assembly connected to the manually rotatable means (to rotate therewith about the axis) and including a cam follower means, and (iii) cam means on the housing positioned to contact and actuate the cam follower means upon rotation of the manually rotatable means, the "actuation" of the cam follower means causing the "ejection" of the PN into the container. Used medical syringes may be stored in the same container, being disposed therein by means including the same manually rotatable means used for used PN disposal.

The invention provides a sharps container which is especially useful for an individual such as a diabetic who may require several daily doses of medication, which doses are required throughout the day (frequently at meal time) and thus may occur at the users residence but are often at other locations such as the user's place of work, at a restaurant, in an automobile or aircraft, etc. The container provided by this invention facilitates disposal of both used PNs and used medical syringes, regard being given to some diabetics daily use of both types of apparatus.

BRIEF DESCRIPTION OF THE DRAWINGS

FIG. 4A is a view very similar to FIG. 4 except showing the rotatable means rotated clockwise so that cam means within the housing has actuated cam follower means of the ejector member to eject a PN into the container.

FIG. 6 is a cross-sectional view of the pen needle ejector assembly (with the elongated ejector member axially displaced to the left of the elongated means) as viewed along section lines 6—6 of FIG. 4.

DETAILED DESCRIPTION OF THE INVENTION

Figure 1:
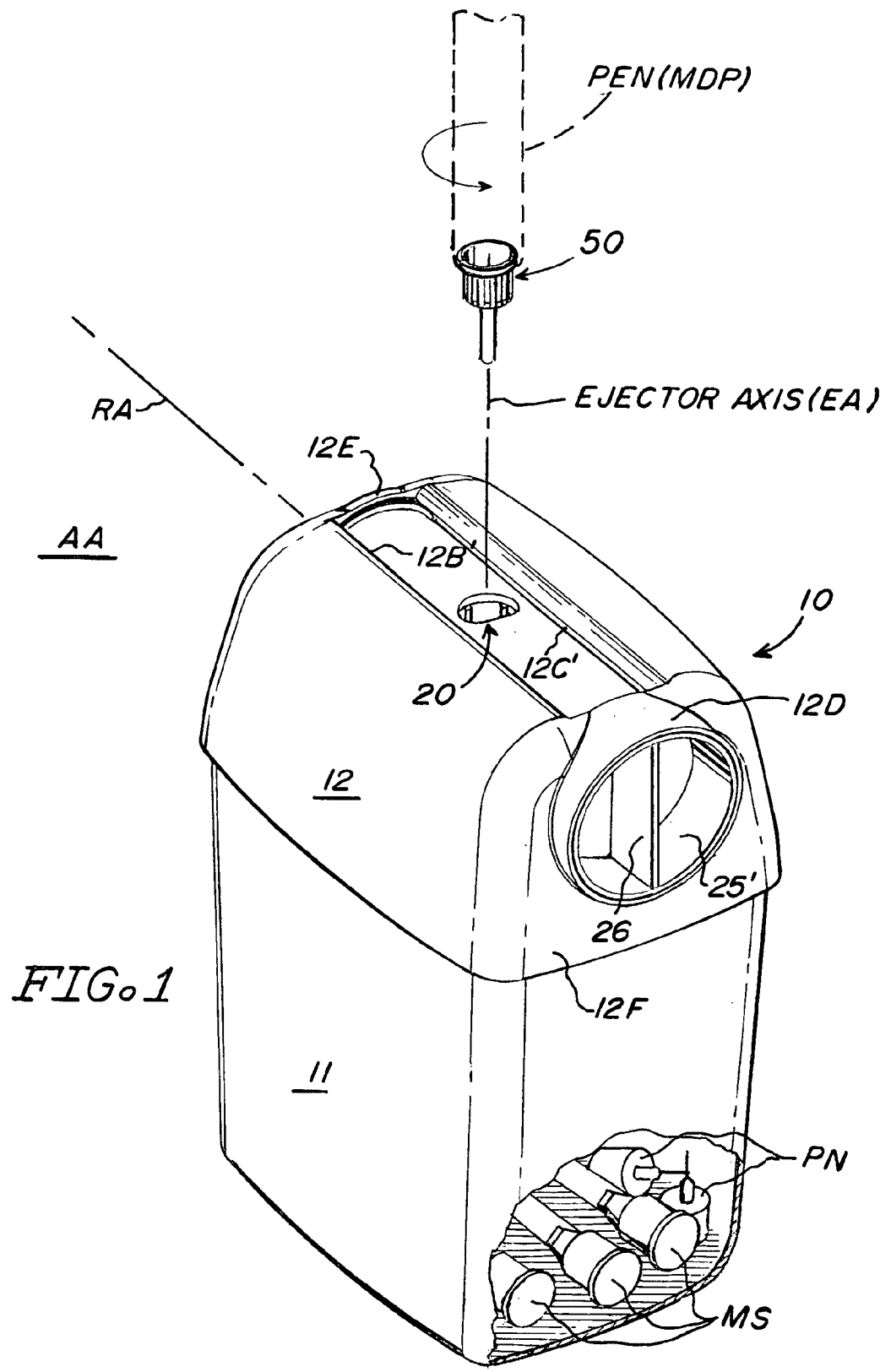
FIG. 1 is a top, side isometric view of the preferred embodiment of the sharps container provided by our invention; this view shows the rotatable means 20 oriented to receive a used PN 50.
Figure 2:
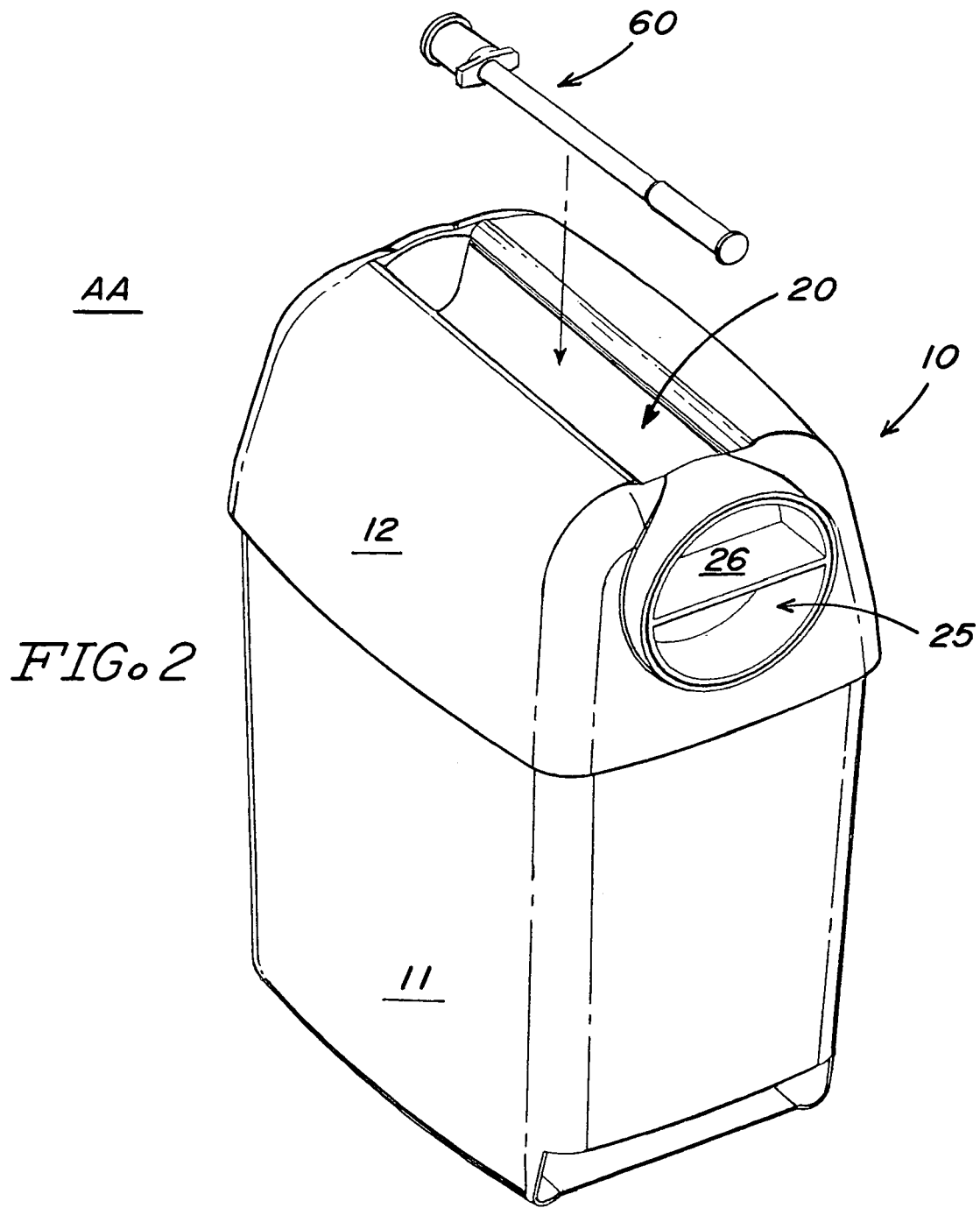
FIG. 2 is an isometric view of the same container shown in FIG. 1 with the rotatable means 20 oriented to receive a used medical syringe 60.

In FIG. 1 a multi-function sharps container AA provides a single apparatus for both the safe, i.e., "no direct human touching" storage of used pen needles and for the safe storage of medical syringes. The container AA comprises a housing 10 having a bottom or storage section 11 and an upper or cover section 12 which fit, and lock, together as is shown clearly in FIGS. 1, 2 and 4A to define an internal storage space sized to facilitate the safe storage of a plurality of used pen needles and medical syringes. Thus section 11 has sides and a bottom surface 11' defining a cup-like means for receiving used pen needles and medical syringes and a top edge with a rim 11A having an outward extending shoulder. Cover section 12 has a longitudinally extending curved cross sectional shape shown in FIGS. 1, 2, 4 and 4A. The top of cover section 12 has a longitudinally extending opening defined by laterally spaced-apart sides 12B' and 12C', the spacing being pre-selected to admit an axially oriented medical syringe 60 as is depicted in FIG. 2.

Importantly, Cover 12 includes an internal partition 12AA having a cam surface means 12AA' (see FIGS. 4 and 4A); the cam surface means 12AA' is positioned for an initial contact with cam follower means 40C (described below) as the rotatable means 20 is rotated and, after additional rotation thereof, cause the ejection of a PN into the container. Cover 12 has a lower, inward extending rim 12A adapted to coact with said shoulder on rim 11A of section 11 to lock the sections 11 and 12 together as shown in FIG. 4A.

Cover 12 also has opposed end portions 12D/12F and 12E/12E' for rotatably supporting a manually rotatable means 20 for rotation about a rotational axis RA. The rotatable means 20 comprises an elongated cylindrically shaped member (see, in particular, FIG. 5) having a central hollow core 21 connected at the ends thereof to bearing elements 20A and 25. Bearing element 20A is supported by cover end portions 12E/12E' and bearing element 25 is supported by cover end portions 12D/12F. Bearing element 25 further serves as a means for manually rotating the rotatable means; it has a circular, longitudinally extending outer rim 25' and a cross rib 26 adapted for engagement by the fingers of a human user for manual rotation of the rotatable means 20.

Figure 3:
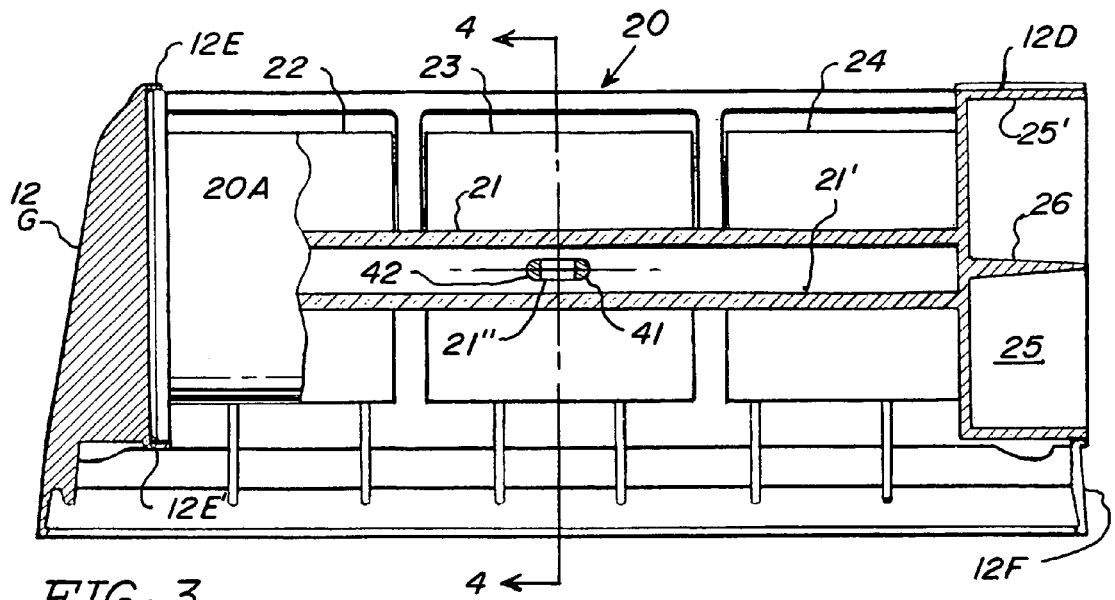
FIG. 3 is a cross-sectional view of the rotatable means.
Figure 4:
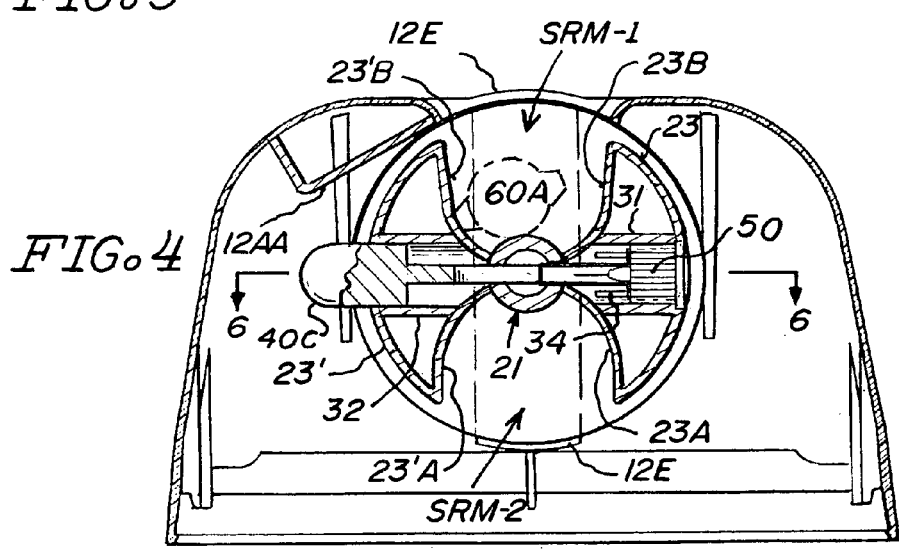
FIG. 4 is a cross-sectional view of the rotatable means as viewed along section lines 4—4 of FIG. 3; this view shows a used pen needle 50 positioned in the pen needle ejector assembly.
Figure 5:
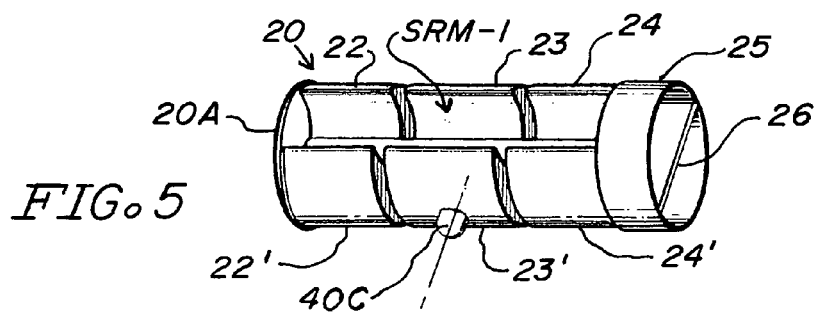
FIG. 5 is an isometric view of the rotatable means.

Integrally connected to the hollow core 21 are three axially aligned sets of fan shaped segments 22/22', 23/23' and 24/24' (see FIGS. 3, 4 and 5). The segments are axially aligned as best shown in FIG. 5. Each segment in said set of segments has exterior curved surfaces concentric with core 21 and extending circumferentially approximately 90 degrees; FIG. 4 shows the opposed curved surfaces 23 and 23'. The rotatable means 20 further includes a pair or opposed, longitudinally extending used syringe receiving means SRM-1 and SRM-2 (see FIGS. 4 and 4A) defined by inwardly extending curved surfaces of segments 22/22', 23/23' and 24/24'; for example FIG. 4 identifies curved surfaces (i) 23A and 23A' and (ii) 23B and 23B' for defining the center (of three) portions of SRM-2 and SRM-1 respectively.

The curved exterior surface of segment 23 has an opening 33 (FIGS. 1 and 6) for admitting the axial insertion of a PN 50 into a pen needle receiving and holding recess 31A described in more detail below. The curved exterior surface of segment 23' has an opening 35 sized to admit the relative axial movement of the cam follower end of an ejector member 40. Openings 33 and 35 define an ejector axis EA (see FIGS. 1 and 6). The ejector assembly further comprises, in part, a pair of axially aligned tubular elements 31 and 32 positioned along the ejector axis EA and connected to and radially extending from core 21 on opposite sides thereof as shown in FIGS. 4 and 6. Core 21 has a pair of aligned, opposed longitudinally elongated slots 21" and 21"' through which spaced-apart legs 41 and 42 on one end of the ejector member 40 are inserted to form the assembly shown in FIGS. 4 and 4A. The ejector member 40 further has a rounded cam follower surface 40C at the other end thereof. The total axial length of ejector member 40 is pre-selected so that the axial ends 41' and 42' of legs 41 and 42 are initially in abutting contact with the radially extending portion of a pen needle positioned in pen needle receiving means 31A in the outboard end of tubular element 31 as is shown in FIG. 4; concurrently the cam follower surface 40C initially extends beyond the surface 23' a pre-selected amount as also is shown in FIG. 4. The legs 41 and 42 have latch means 41" and 42" respectively which, after insertion of the legs through slots 21" and 21"', coact with shoulder means 31' at the inner end of tubular element 31 to hold member 40 in assembled relation with member 20.

Pen needle receiving means 31A includes a plurality of inwardly extending ribs 34 for gripping an inserted PN and preventing rotation of the PN about the ejector axis EA.

FIG. 1 shows, in phantom, a medical delivery pen (MDP) of the well known types currently used having at the distal end thereof male thread means for attachment to female threads in the proximal end of a pen needle 50. It should be understood that pen needle 50 shown in FIG. 1 has already been used and the user desires to safely remove the used pen needle from the pen and thence place the used pen needle into safe storage means. The pen needle 50 has a cylindrical surface 51 with a pre-selected outer diameter. The cylindrical surface 51 also has a plurality of longitudinally extending shallow grooves 54 which co-act with ribs 34 of the pen needle receiving recess 31A to hold the pen needle against rotation about its longitudinal axis when the user unscrews the MDP therefrom.

Operation

To safely dispose and store a used PN, the user would hold the MDP to axially guide the attached PN 50 through opening 33 of the rotatable means 20 into recess 31A of the pen needle receiving and ejecting means, the coacting ribs 34 and shallow slots 54 preventing rotation of the PN about the ejector axis EA to thus facilitate the manual unscrewing of the MDP from the PN. FIG. 4 shows a PN in recess 31A, the rotatable means 20 having been rotated 90 degrees clockwise following the insertion of the PN into the recess. At this orientation the rounded cam follower end 40C is approaching the housing cam means 12 AA'; continued clockwise rotation of the rotatable means 20 brings end 40C into contact with cam means 12 AA' to initiate axial movement of the ejector member 40 along the ejector axis EA to the right as shown in FIG. 4, said axial movement being transferred by the end surfaces 41' and 42' of member 40 to the PN. As the clockwise rotation continues to the position shown in FIG. 4A the ejector member 40 has moved axially sufficiently to eject the PN into the container as is also depicted in FIG. 4A.

Additional used pen needles may be sequentially safely disposed and stored by following the same procedure. The rotatable means 20 is oriented with the opening 33 in the position shown in FIG. 1.

To safely dispose and store a medical syringe, the rotatable means 20 is oriented with one of the syringe receiving means SRM-1 or SRM-2 in the position shown in FIG. 4, i.e. with a SRM in register with the cover opening defined by cover edges 12B' and 12C'. Then, as depicted in FIG. 2, the used syringe 60 is placed into the SRM. Next the rotatable means 20 is rotated manually either direction sufficiently for the used syringe to fall away and down into the storage area of the section 111 of the container. FIG. 4A depicts the clockwise rotation of the rotatable means 20 carrying a used syringe 60A positioned in SRM-1; continued clockwise rotation would discharge the syringe into section 11 of the container.

Thus the user of medical syringes and pen needles has a single container for the safe disposal and storage of both sharps after the use thereof. It will be understood that the pen user does not have to touch the used pen needle either to (i) remove the used pen needle from the pen, or (ii) dispose the used pen needle into a safe storage means. The medical syringe receiving and disposal means provided by our invention maximizes the safety for the user.

While we have shown our preferred embodiment of the invention, it will be understood that variations may be made without departing from the inventive concept.

For example, while the pen needle ejector mechanism has been positioned within a tubular means, other means may provide an elongated bore means within which the ejector mechanism is positioned.

Also, the syringe receiving means SRM-1 and SRM-2 may, besides the specifically described function of receiving medical syringes (MSs), may also be used to receive used pen needle assemblies (PNAs) for disposal into the container. Accordingly, the invention is to be limited only by the scope of the following claims.

What is claimed is:

1. A sharps container for facilitating (i) the safe manual, sequential, selective insertion of cylindrically shaped used pen needles directly from a medical delivery pen into said container for safe storage therein, said pen needles having a pre-selected outer diameter, and (ii) the insertion, for safe disposal, of used medical syringes into said container, said container comprising:
   A. housing means with an internal storage space sized to facilitate the safe storage therein of a plurality of used pen needles and used medical syringes;
   B. used pen needle receiving and ejecting means connected to said housing means and including:
      (1) manually rotatable means connected to said housing means for rotation relative to said housing means about a rotational axis,
      (2) a pen needle ejector assembly having an ejector axis and connected to said rotatable means to be rotated thereby about said rotational axis, said ejector assembly comprising (i) elongated means having receiving means at a first end thereof sized to receive a used pen needle and (ii) an elongated ejector member connected to said elongated means for relative axial movement therewith and having (a) cam follower means at one end thereof initially positioned a pre-selected axial distance along said ejector axis beyond a second end of said elongated means, and (b) a second end initially positioned adjacent said used pen receiving means, and
      (3) cam means within said housing positioned for an initial contacting of said cam follower means when said rotatable member and said ejector assembly is rotated about said rotational axis; and
   C. used medical syringe receiving and disposal means comprising means included in said rotatable means (i) for receiving a used medical syringe, and (ii) following a pre-selected rotation of said rotatable means about said rotational axis, for disposing said used medical syringe into said container storage space,
   whereby, (a) when a used pen needle is positioned in said pen needle receiving means and said manually rotatable means is rotated a pre-selected amount about said rotational axis from said position of said initial contacting so that said cam follower means progressively contacts said cam means to move said ejector means along said ejector axis to force said used pen needle axially out of said pen needle receiving means into said container storage space, and (b) when a used medical syringe is received by said means included in said rotatable means for receiving a used medical syringe and said rotatable means is rotated said pre-selected rotation about said rotational axis, said used medical syringe will be disposed into said container storage space.

2. The sharps container of claim 1 further characterized by said manually rotatable means comprising (i) an elongated cylindrically shaped member supported on opposite ends thereof on said housing means and disposed in an elongated opening in said housing sized to receive said elongated cylindrically shaped member, and (ii) at least one elongated recess in said elongated cylindrically shaped member sized to receive at least one used medical syringe.

3. The sharps container of claim 2 including said used pen needle ejector assembly being mounted on said elongated cylindrically shaped member with said ejector axis being oriented at an angle to said rotational axis.

4. The sharps container of claim 3 wherein (i) said elongated cylindrically shaped member has two of said elongated recesses disposed longitudinally on opposite sides of said rotational axis, and (ii) said used pen needle ejector assembly is mounted, as aforesaid, so that said ejector axis is normal to said rotational axis.

5. The sharps container of claim 4 further characterized by said elongated means of said ejector assembly including two, axially aligned and axially spaced apart tubular means connected to said elongated cylindrically shaped member and having bore means for receiving said ejector member.

6. The sharps container of claim 5 wherein a first of said tubular means has recessed means at an end thereof sized to receive a used pen needle.

7. The sharps container of claim 4 wherein said cylindrically shaped member has a longitudinally extending central core portion including a central means for supporting said elongated ejector member for movement, relative to said cylindrically shaped member, along said ejector axis.

8. The sharps container of claim 7 wherein said cylindrically shaped member includes first and second axially aligned and axially spaced apart tubular means axially aligned with and on opposite sides of said central means, said tubular means having bore means for receiving said elongated ejector member, and said first of said tubular means having means for receiving a used pen needle.

9. The sharps container of claim 8 wherein said elongated ejector member is initially positioned, for relative axial motion along said ejector axis relative to said aligned central means and said first and second tubular means, so that (i) said cam follower means is positioned a pre-selected distance beyond said second of said tubular means, and (ii) said second end of said ejector member is positioned adjacent to said means for receiving a used pen needle.

10. The sharps container of claim 9 wherein said second end of said elongated ejector member includes means for accommodating an axially extending used needle attached to a pen needle positioned in said used needle receiving means.

11. The sharps container of claim 2 wherein said rotatable cylindrically shaped member is characterized so that said at least one elongated recess is parallel to said rotational axis and is adapted, when in a first angular orientation relative to said housing means, to receive a used medical syringe and is adapted, when in a second angular position relative to said housing means, to dispose of said used medical syringe into said container.

12. The sharps container of claim 1 wherein said receiving means comprises recess means having a plurality of axially extending ribs.

13. The sharps container of claim 4 wherein said ejector axis is positioned intermediate said two longitudinally disposed recesses.

14. The sharps container of claim 9 wherein said second end of said elongated ejector member comprises two axially extending legs laterally spaced-apart a pre-selected distance for permitting the unobstructed positioning therebetween of a used needle of a pen needle received by said used pen needle receiving means.

15. The sharps container of claim 9 including means on said elongated ejector member for limiting the axial displacement of said cam follower means beyond said pre-selected axial distance along said ejector axis.

16. The sharps container of claim 15 wherein said means for limiting axial displacement of said cam follower means includes (i) a pair of spaced apart legs integral with said elongated ejector member, and (ii) shoulder means on said housing means.

\* \* \* \* \*